US00PP14101P29

(12) United States Plant Patent
Klemm

(10) Patent No.: US PP14,101 P2
(45) Date of Patent: Aug. 26, 2003

(54) GERANIUM PLANT NAMED 'KLEP01110'

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 10/259,974

(22) Filed: Sep. 29, 2002

(51) Int. Cl.[7] ..... A01H 5/00

(52) U.S. Cl. ..... Plt./329

(58) Field of Search ..... Plt./329

*Primary Examiner*—Kent Bell
(74) *Attorney, Agent, or Firm*—C. A. Whealy

(57) ABSTRACT

A new and distinct cultivar of Zonal Geranium plant named 'KLEP01110' characterized by its upright and outwardly spreading plant habit; freely branching and flowering habit; early flowering habit; red purple-colored flowers arranged in rounded umbels held above the foliage on upright and strong peduncles; and good tolerance to rain and high temperatures.

1 Drawing Sheet

BOTANICAL CLASSIFICATION/CULTIVAR DESIGNATION

*Pelargonium×hortorum* cultivar 'KLEP01110'.

BACKGROUND OF THE INVENTION

The present invention relates to a new and distinct cultivar of Zonal Geranium plant, botanically known as *Pelargonium×hortorum,* and hereinafter referred to by the name 'KLEP01110'.

The new Zonal Geranium is a product of a planned breeding program conducted by the Inventor in Stuttgart, Germany. The objective of the breeding program was to develop new Zonal Geraniums with uniform plant habit and interesting flower and foliage colors.

The new Zonal Geranium originated from a cross-pollination made by the Inventor in 1997 of the *Pelargonium×hortorum* cultivar 'Klecona', disclosed in U.S. Plant patent application Ser. No. 09/250,015, (now abondoned) as the female, or seed, parent with the *Pelargonium×hortorum* cultivar. 'Klecardi', not patented, as the male, or pollen, parent. The cultivar KLEP01110 was discovered and selected by the Inventor as a flowering plant within the progeny from this cross-pollination in a controlled environment in Stuttgart, Germany, in June, 1998.

Asexual reproduction of the new cultivar by terminal cuttings taken in a controlled environment in Stuttgart, Germany since 1999 has shown that the unique features of this new Zonal Geranium are stable and reproduced true to type in successive generations of asexual reproduction.

SUMMARY OF THE INVENTION

The following traits have been repeatedly observed and are determined to be the unique characteristics of 'KLEP01110'. These characteristics in combination distinguish 'KLEP01110' as a new cultivar and distinguish it from other known Zonal Geranium cultivars:

1. Upright and outwardly spreading plant habit.
2. Freely branching and flowering habit.
3. Early flowering habit.
4. Red purple-colored flowers arranged in rounded umbels held above the foliage on upright and strong peduncles.
5. Good tolerance to rain and high temperatures.

Plants of the new Zonal Geranium are most similar to plants of the female parent, the cultivar Klecona. Plants of the new Zonal Geranium differ from plants of the cultivar Klecona in the following characteristics:

1. Plants of the new Zonal Geranium are larger and more vigorous than plants of the cultivar Klecona.
2. Leaves of plants of the new Zonal Geranium do not have a zonation pattern whereas leaves of plants of the cultivar Klecona have a zonation pattern.
3. Plants of the new Zonal Geranium have larger flowers than plants of the cultivar Klecona.

Plants of the new Zonal Geranium differ from plants of the male parent, the cultivar Klecardi, in the following characteristics:

1. Plants of the new Zonal Geranium are larger and more vigorous than plants of the cultivar Klecardi.
2. Leaves of plants of the new Zonal Geranium do not have a zonation pattern whereas leaves of plants of the cultivar Klecardi have a zonation pattern.
3. Plants of the new Zonal Geranium and the cultivar Klecona differ in flower coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal Geranium. The photograph comprises a side perspective view of a typical flowering plant of 'KLEP01110' grown in a 12-cm container.

DETAILED BOTANICAL DESCRIPTION

Plants of the cultivar KLEP01110 have not been observed under all possible environmental conditions. The phenotype may vary somewhat with variations in environment, such as temperature and light intensity, without, however, any variance in genotype.

The aforementioned photograph, following observations, and averaged measurements describe plants that were planted in January in 12-cm pots in Stuttgart, Germany, and grown under commercial practice in a glass-covered greenhouse with day temperatures ranging from 18 to 22° C., night temperatures ranging from 14 to 16° C., and light levels ranging from 20,000 to 55,000 lux. The photograph and information for the detailed botanical description were taken about 3.5 months after planting rooted young plants.

In the following description, color references are made to The Royal Horticultural Society Colour Chart, 1995 Edition, except where general terms of ordinary dictionary significance are used.

Botanical classification: *Pelargonium×hortorum* cultivar KLEP01110.

Parentage:

*Female Parent.*—*Pelargonium×hortorum* cultivar Klecona, disclosed in U.S. Plant patent application Ser. No. 09/250,015 (now abandoned).

*Male parent.*—*Pelargonium×hortorum* cultivar Klecardi, not patented.

Propagation:

*Type cutting.*—Terminal cuttings.

*Time to initiate roots.*—Summer: About 10 days at 22° C. Winter: About 12 days at 18 to 20° C.

*Time to produce a rooted young plant.*—Summer: About 16 days at 22° C. Winter: About 18 days at 18 to 20° C.

*Root description.*—Fine, freely branching, and white in color.

Plant description:

*General appearance.*—Upright and outwardly spreading plant habit; densely foliated.

*Growth and branching habit.*—Moderately vigorous. Freely branching, about four or five lateral branches develop without pinching, that is, removal of terminal apices.

*Plant height* (*to top of flower umbels*).—About 25 to 28 cm.

*Plant height* (*to top of foliar plane*).—About 17 to 21 cm.

*Plant width.*—About 24 to 27 cm.

*Lateral branches.*—Length: About 8 to 10 cm. Internode length: About 1.5 to 2 cm. Texture: Pubescent. Color: 139C.

*Foliage description.*—Arrangement: Alternate, simple. Length: About 8 to 12 cm. Width: About 8 to 11 cm. Shape: Rounded, reniform. Apex: Rounded. Base: Lobed, not overlapping. Margin: Crenate, lobed. Venation pattern: Palmate. Texture: Pubescent; rough. Color: Young and fully expanded foliage, upper surface: 137A; no distinct zonation pattern. Young and fully expanded foliage, lower surface: 137C. Venation, upper surface: 139C. Venation, lower surface: 139B. Petiole: Length: About 5 to 6 cm. Diameter: About 4 to 5 mm. Color, upper and lower surfaces: 139C.

Flower description:

*Flower arrangement.*—Red purple-colored flowers arranged in rounded hemispherical umbels arising from apical leaf axils. Umbels displayed above the foliage on upright and strong peduncles. Flowers double in form, rounded and cup-shaped. Umbels persistent, flowers not persistent. Flowers not fragrant.

*Quantity of flowers.*—Freely flowering habit; at full flower, plants have at least about 8 to 10 open and developing umbels with about 30 to 40 flowers and flower buds per umbel.

*Flowering season.*—Year-round under greenhouse conditions. In the garden, flowering is continuous from spring until fall.

*Time to flower.*—Early flowering; plants start flowering about 80 days after planting rooted young plants.

*Flower longevity.*—Flowers last about 6 to 12 days on the plant.

*Umbel size.*—Height: About 10 to 12 cm. Diameter: About 8 to 12 cm.

*Flower size.*—Diameter: About 5 to 6 cm. Depth (height): About 1.5 to 2 cm.

*Flower buds.*—Length: About 1 to 1.5 cm. Diameter: About 6 to 8 mm. Shape: Elliptical. Color: 139C.

*Petals.*—Quantity per flower: About 6 to 7. Length: About 2.5 cm. Width: About 2 cm. Shape: Ovate. Apex: Rounded. Base: Attenuate. Margin: Entire. Texture, upper and lower surfaces: Smooth, velvety. Color: When opening, upper surface: 57A. When opening, lower surface: 58B. Fully opened, upper surface: 57B, towards base, 58C; color becoming closer to 57A with development. Fully opened, lower surface: 58B, towards base, 58C. Venation, upper and lower surfaces: 57A.

*Petaloids.*—Quantity per flower: None to about six. Length: About 3 to 10 mm; irregular in size. Width: About 3 to 8 mm; irregular in size. Shape: Variable, irregular. Apex: Mostly rounded. Base: Attenuate. Margin: Mostly entire. Texture, upper and lower surfaces: Smooth, velvety. Color: When opening and fully opened, upper surface: 57B, towards base, 58C; color does not fade with development. When opening and fully opened, lower surface: 58B, towards base, 58C. Venation, upper and lower surfaces: 57B.

*Sepals.*—Quantity per flower: Five, arranged in a single whorl. Length: About 8 to 10 mm. Width: About 4 to 6 mm. Shape: Elliptical. Apex: Acute. Margin: Entire. Texture, upper and lower surfaces: Pubescent, velvety. Color, upper surface: 141C. Color, lower surface: 141D.

*Peduncle* (*umbel stem*).—Length: About 15 to 18 cm. Diameter: About 5 to 6 mm. Angle: Erect. Strength: Strong. Texture: Pubescent; rough. Color: 139C.

*Pedicel* (*individual flower stem*).—Length: About 2.5 cm. Diameter: About 1.5 mm. Angle: Erect. Strength: Moderately strong. Texture: Pubescent; rough. Color: 139D overlain with 180C.

*Reproductive organs.*—Androecium: Anther quantity per flower: Five. Anther length: About 3 mm. Anther shape: Ovate. Anther color: 58C. Pollen amount: Moderate. Pollen color: 35A. Gynoecium: Pistil quantity per flower: One. Pistil length: About 8 to 10 mm. Stigma shape: Five-parted, star-shaped. Stigma color: 58D. Style length: About 3 to 5 mm. Style color: 58D. Ovary color: 149D.

*Seed.*—Length: About 3 to 6 mm. Diameter: About 1.5 to 2 mm. Shape: Ovoid. Color: Brownish.

Disease/pest resistance: Plants of the new Zonal Geranium have not been observed to be resistant to pathogens and pests common to Zonal Geraniums.

Weather tolerance: Plants of the new Zonal Geranium have been observed to tolerate rain, wind, and temperatures from about 8 to 32° C. and have good garden performance.

It is claimed:

1. A new and distinct cultivar of Zonal Geranium plant named 'KLEP01110', as herein illustrated and described.

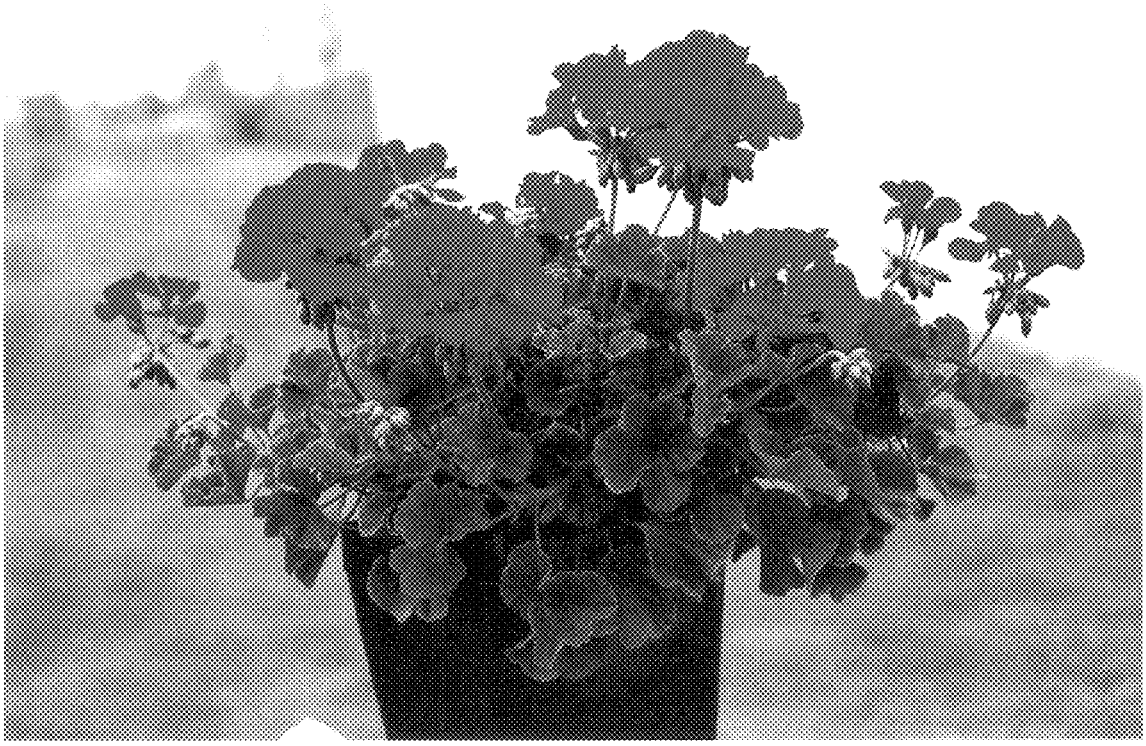

* * * * *